United States Patent [19]

Haferl

[11] Patent Number: 4,572,993
[45] Date of Patent: Feb. 25, 1986

[54] TELEVISION DEFLECTION CIRCUIT WITH RASTER WIDTH STABILIZATION

[75] Inventor: Peter E. Haferl, Adliswil, Switzerland

[73] Assignee: RCA Corporation, Princeton, N.J.

[21] Appl. No.: 651,316

[22] Filed: Sep. 17, 1984

[30] Foreign Application Priority Data

Dec. 12, 1983 [GB] United Kingdom ............... 8333067

[51] Int. Cl.⁴ .................. H01J 29/70; H01J 29/76
[52] U.S. Cl. .................. 315/408; 315/370; 315/411
[58] Field of Search .......... 315/399, 408, 411, 370; 358/190

[56] References Cited

U.S. PATENT DOCUMENTS 4,104,567  8/1978  Peer et al. ............... 315/387
4,209,732  6/1980  Smith ..................... 315/400
4,298,829 11/1981  Luz ....................... 315/308

FOREIGN PATENT DOCUMENTS 59-110276  6/1984  Japan .

OTHER PUBLICATIONS

U.S. patent application, filed Dec. 23, 1983, Ser. No. 564,912, entitled, Television Receiver Load Compensation Circuit in the name of P. E. Haferl.

Primary Examiner—Theodore M. Blum
Attorney, Agent, or Firm—Eugene M. Whitacre; Joseph J. Laks; Sammy S. Henig

[57] ABSTRACT

An energizing voltage is series coupled with a diode, an inductor, a flyback transformer primary winding and an input terminal of a deflection circuit. During trace, the diode is forward biased causing a voltage to be developed across and an input current to flow in the inductor. During retrace, opposite polarity retrace voltage commutates off the diode and decouples the input terminal from the energizing voltage at a varied instant within retrace, in accordance with the amplitude of the input current. The amplitude of the input current is related to the ultor load current. A voltage that is indicative of the input current is developed across a capacitor. A DC voltage between one plate of the capacitor and a reference conductor controls the deflection current in the deflection winding such that variations in the ultor voltage produce the same sense variations in the DC voltage that is supplied by the capacitor for maintaining a substantially constant raster width.

20 Claims, 5 Drawing Figures

DEFLECTION CIRCUIT 200'

DEFLECTION CIRCUIT 200''

TELEVISION DEFLECTION CIRCUIT WITH RASTER WIDTH STABILIZATION

This invention relates to regulation of the raster size of a television scanning system when the accelerating potential in a television receiver vary.

The accelerating potential, or the ultor voltage for the electron beams of a cathode ray tube of a television receiver is obtained from the high voltage circuit of the horizontal output transformer. The width of each horizontal raster line will vary with variations in accelerating potential, the width increasing with decreasing ultor voltage. This effect is commonly called breathing. Decreasing ultor voltage can be caused by heavy beam current loading of the high voltage circuit of the output transformer as a result of heavy video loading.

Raster line width is also determined by the magnitude of the voltage applied across the horizontal deflection winding during the trace interval of the deflection cycle, the width of the raster line decreasing with decreasing voltage applied across the winding. The voltage across the winding is frequently derived from a regulated voltage coupled to the horizontal deflection circuit. Heavy video loading will result in an increased load current being drawn from the regulated voltage source by the high voltage circuit.

To compensate for the effects of breathing, prior art circuits, such as disclosed in U.S. Pat. No. 3,444,426, granted to M. E. Buechel, have placed a resistance in series with the load comprising the horizontal output stage. The increased voltage drop across the resistance as heavy video loading occurs, decreases the voltage across the deflection winding, thereby decreasing the raster line width. Such raster line width regulation, however, undesirably increases power dissipation. In other prior art circuits, such as disclosed in U.S. Pat. No. 4,104,567, granted to Peer et al., the load current is sensed by an error amplifier that controls the turn on time of an SCR. The conduction times of the SCR is controlled in response to variations of load current to control the magnitude of the energizing voltage to the deflection circuit for maintaining a substantially constant raster width.

In accordance with an aspect of the invention, a deflection system includes a deflection winding coupled to a deflection generator that generates trace and retrace scanning currents in the deflection winding. A transformer that includes first and second transformer windings, in which an alternating current deflection rate voltage is developed, is coupled to the deflection generator. An ultor circuit draws load current from the second transformer winding. An inductance, across which a voltage that corresponds to the load current is developed, is coupled to the transformer. A first voltage is developed from the voltage across the inductance at a terminal of the first transformer winding to control the amplitude of the trace scanning current, wherein different values of the load current produce different values of voltage across the inductance for stabilizing the raster width.

Variations of beam current loading applied by the ultor circuit may cause corresponding variations of the retrace interval. For example, an increase of beam current that may cause a decrease in ultor voltage may cause an increase in the retrace interval and a corresponding increase in the raster width. It is desirable to maintain a constant retrace interval when the magnitude of the beam current changes. Accordingly, a feature of the invention is that variations of the retrace interval, that may be caused by the corresponding variations of beam current are reduced. Reducing the variations of the retrace interval is accomplished by modulating the inductance that is coupled across the deflection winding. Thus, the circuit of the invention maintains a substantially constant raster width and retrace interval.

Figure 1:
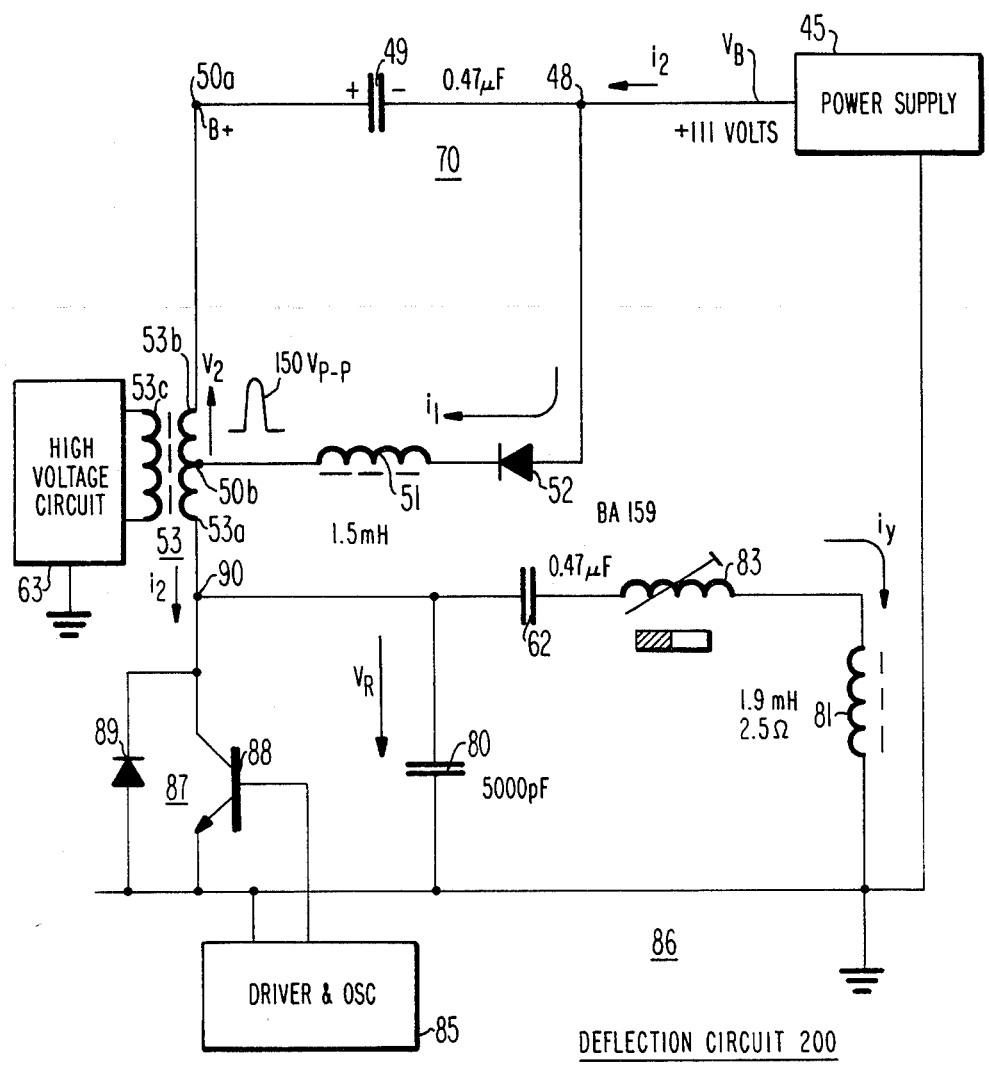
FIG. 1 illustrates a deflection circuit embodying the invention.

In a deflection circuit 200, illustrated in FIG. 1, a filtered DC voltage $V_B$ is developed at a terminal 48. Voltage $V_B$ is supplied by a power supply 45 that may be of the switching mode type. A raster width control circuit 70, embodying one aspect of the invention, is coupled between terminal 48 and terminals 50a and 50b, respectively, of horizontal deflection circuit 200 for developing a boosted voltage B+ at input terminal 50a. Input terminal 50a is coupled through series coupled primary windings 53b and 53a of a horizontal output flyback transformer 53 to a horizontal deflection generator 86 of horizontal deflection circuit 200. Illustratively, the turns ratio of windings 53b and 53a is 15:85 and the combined inductance is 5 mH. Terminal 50b is coupled to the junction between primary windings 53b and 53a of flyback transformer 53.

A horizontal deflection winding 81 is coupled to horizontal deflection generator 86. Generator 86 comprises a linearity inductor 83 and a trace capacitor 62 that are series coupled to deflection winding 81, a retrace capacitor 80, and a trace switch 87 comprising a horizontal output transistor 88 and a damper diode 89 for generating scanning current in deflection winding 81 each horizontal deflection cycle. Horizontal deflection generator 86 is coupled to a terminal 90 of primary winding 53a of flyback transformer 53. A conventional synchronized horizontal oscillator and driver circuit 85 provides switching control signals to the control base electrode of horizontal output transistor 88 to turn on the transistor during the horizontal trace interval and to turn off the transistor for initiating the horizontal retrace interval. A high voltage winding 53c of flyback transformer 53 is coupled to a conventional high voltage circuit 63 for developing an ultor accelerating potential for beam current.

Raster width control circuit 70 includes an inductor 51 and a rectifier diode 52 series coupled between terminal 48 and terminal 50b, a tap of the primary winding of flyback transformer 53. Raster width control circuit 70 also includes a capacitor 49 coupled between terminal 48, the output terminal of voltage source 45, and terminal 50a, the low side of the primary winding of flyback transformer 53.

In operation, deflection switch 87 is closed during the trace interval. When deflection switch 87 is closed, it isolates transformer 53 from deflection circuit 86. An upramping primary current $i_2$ in primary windings 53a and b increases the energy stored in flyback transformer 53 during the trace interval. This stored energy replenishes losses in deflection circuit 86 and energizes high voltage circuit 63, during the retrace interval, when switch 87 is opened. Deflection generator 86 forms with transformer 53 a retrace resonant circuit. The energy stored in transformer 53 and deflection winding 81, during the trace interval, is transferred into retrace capacitor 80 to produce a retrace voltage $V_R$ across capacitor 80, during the retrace interval.

Figure 2:
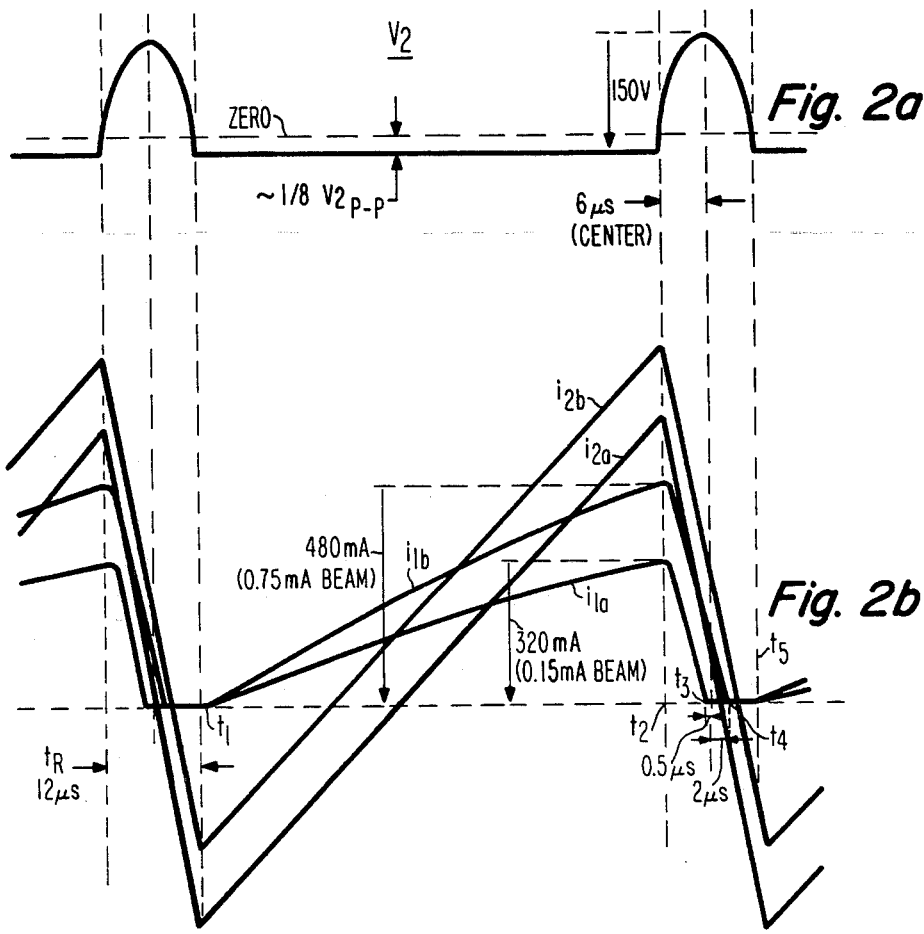
FIGS. 2a and 2b illustrate, respectively, waveforms useful in explaining the deflection circuit of FIG. 1.

FIG. 2a illustrates the waveform of voltage $V_2$ across primary winding 53b. Voltage $V_2$ comprises a retrace pulse during the retrace interval t2 to t5. FIG. 2b illustrates a first example of the waveform of current $i_{1a}$ in inductor 51 and the current $i_{2a}$ in transformer winding 53a under conditions of a relatively low ultor beam current. FIG. 2b also illustrates a second example of the waveform of current $i_{1b}$ in inductor 51 and the associated current $i_{2a}$ in transformer winding 53a under conditions of an ultor beam current that is higher than in the first example.

Assuming hypothetically that inductor 51 has zero inductance. In such a hypothetical case, capacitor 49 is charged to approximately the voltage level of voltage $V_2$ during the trace interval. As illustrated in the example of FIG. 2a, trace voltage $V_2$ is approximately equal to $\frac{1}{8}$ of the peak to peak voltage of voltage $V_2$ during the retrace interval. Terminal 50a has a higher potential than terminal 50b, and the voltage across capacitor 49 is added serially to voltage $V_B$ to produce boosted voltage B+.

In circuit 200 of FIG. 1 inductor 51 has in fact a non-zero inductance. Therefore, the voltage across capacitor 49 becomes a function of the load current in high voltage circuit 63. Also, during the retrace interval, raster width circuit 70 acts as an inductance that is modulated by the load current in high voltage circuit 63, as described in detail later on.

During the retrace interval, the polarity of retrace voltage $V_2$ is such that current $i_1$ becomes progressively smaller. When the voltage across diode 52 reverses polarity, at some point during the retrace interval, current $i_1$ stops flowing.

The rate of change $di_2/dt$ of transformer primary current $i_2$, for example, is controlled by voltage B+, during the trace interval t1 to t2 of FIG. 2b; it is controlled by voltage $V_R$ of FIG. 1, during the retrace interval. The rate of change $di_2/dt$ is not substantially affected by the high voltage beam current. An increase of the high voltage beam current in circuit 63 of FIG. 1 causes a corresponding increase in current $i_1$. Because current $i_1$ begins as zero current, at the beginning of the trace interval t1 of FIG. 2b, its rate of change $di_1/dt$ is a function of the beam current. As illustrated in the first and second examples of FIG. 2b, $di_{1a}/dt$ during the trace interval is lower than $di_{1b}/dt$. The rate of change $di_1/dt$, during the trace interval t1 to t2, is controlled by the voltage across inductor 51 of FIG. 1. Because trace voltage $V_2$ is relatively independent of the beam current, the voltage across capacitor 49 decreases when the beam current increases so that the voltage across inductor 51 may increase. Conversely, when the beam current decreases, the voltage across inductor 51 decreases and the voltage across capacitor 49 increases.

The voltage across capacitor 49 is added in series to voltage $V_B$ to provide boosted voltage B+. Without any load and circuit losses, current $i_1$ is substantially zero and capacitor 49 charges to the trace voltage $V_2$. At high level of current $i_1$, the entire trace voltage $V_2$ is developed across inductor 51 and the voltage across capacitor 49 is zero. Therefore, boosted voltage B+ varies between voltage $V_B$, corresponding to high level of beam current, and voltage $V_B$ plus the trace voltage $V_2$, corresponding to zero beam current. Moving tap 50b of transformer 53 toward terminal 90 causes an increase in trace voltage $V_2$, provides a wider variation range of voltage B+ and causes an increase in the contribution of inductor 51 to the inductance of transformer 53 that is coupled during the retrace interval, as described later on.

When the ultor current increases, resulting in decreasing ultor voltage, voltage B+ decreases. Voltage B+ controls the amplitude of trace current $i_y$ in deflection winding 81. This is so because the voltage across trace capacitor 62 that generates trace current $i_y$ is equal approximately to voltage B+. Consequently, an increase in the ultor current, that causes a corresponding increase in current $i_1$ and that is accompanied by a decrease in the ultor voltage, causes a corresponding decrease in voltage B+. The decrease in voltage B+ tends to stabilize the width of the raster, as explained before.

At the end of the trace interval time t2 of FIG. 2b, the energy stored in inductor 51 of FIG. 1 is beam current dependent. Therefore, diode 52 remains conductive for a certain duration during the retrace interval which is also beam current dependent: in the first example of low beam current loading—until time t3 of FIG. 2b, and in the second example of high beam current loading—until a later time t4.

During the period in which diode 52 of FIG. 1 is conductive, in the retrace interval, inductor 51 is parallel coupled to winding 53b of transformer 53 causing that the inductance of the primary winding coupled to terminal 90 is lower. This lowering of the inductance of the primary winding results in a higher retrace resonance frequency and a corresponding shortening of the retrace interval. The longer diode 52 conducts during the retrace interval, the higher is the retrace resonance frequency.

Thus, the beam current load tends to cause modulation of the retrace interval. This modulation compensates for the tendency of the retrace interval to increase when the beam current increases when no compensation scheme such as raster width control circuit 70 is employed. Such increase in the retrace interval occurs because the capacitive load of the picture tube that is coupled to high voltage circuit 63 loads the retrace resonance circuit of deflection circuit 86.

Advantageously, the raster compensation is obtained by using reactive components, rather than resistive loads; therefore, the corresponding energy loss in circuit 200 of FIG. 1 is low. The passive control of both voltage B+ and the modulated inductance of circuit 70 results in substantially constant raster width over the entire range of beam current. The fast response time of circuit 70 has the added advantage of improved white bar performance of the screen display.

In the first example of low beam current loading, in which current $i_1 = i_{1a}$, with voltage $V_B$ being 111 volts, the following are illustrative values of the circuit of FIG. 1: voltage B+ = 118 volts, voltage $V_R$ = 1040 volts, retrace interval $t_R$ = 11.8 microseconds, peak to peak deflection current $i_y$ = 3.15 amperes and the ultor voltage = 24.4 KV. In the second example of high beam current loading, in which current $i_1 = i_{1b}$, with voltage $V_B$ being the same 111 volts, the following are illustrative values of the circuit of FIG. 1: voltage B+ = 111 volts, voltage $V_R$ = 920 volts, retrace interval $t_R$ = 12 microseconds, peak to peak deflection current $i_y$ = 2.9 amperes and the ultor voltage = 21.7 KV.

Figure 3:
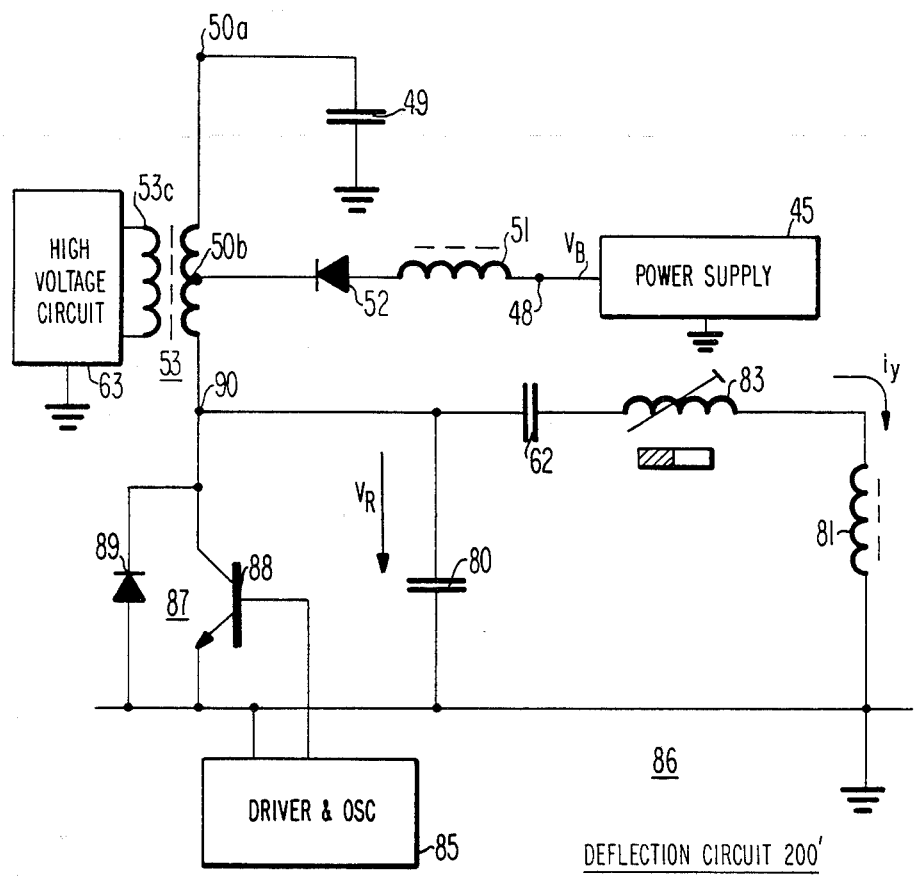
FIG. 3 illustrates a second embodiment of a deflection circuit embodying the invention.
Figure 4:
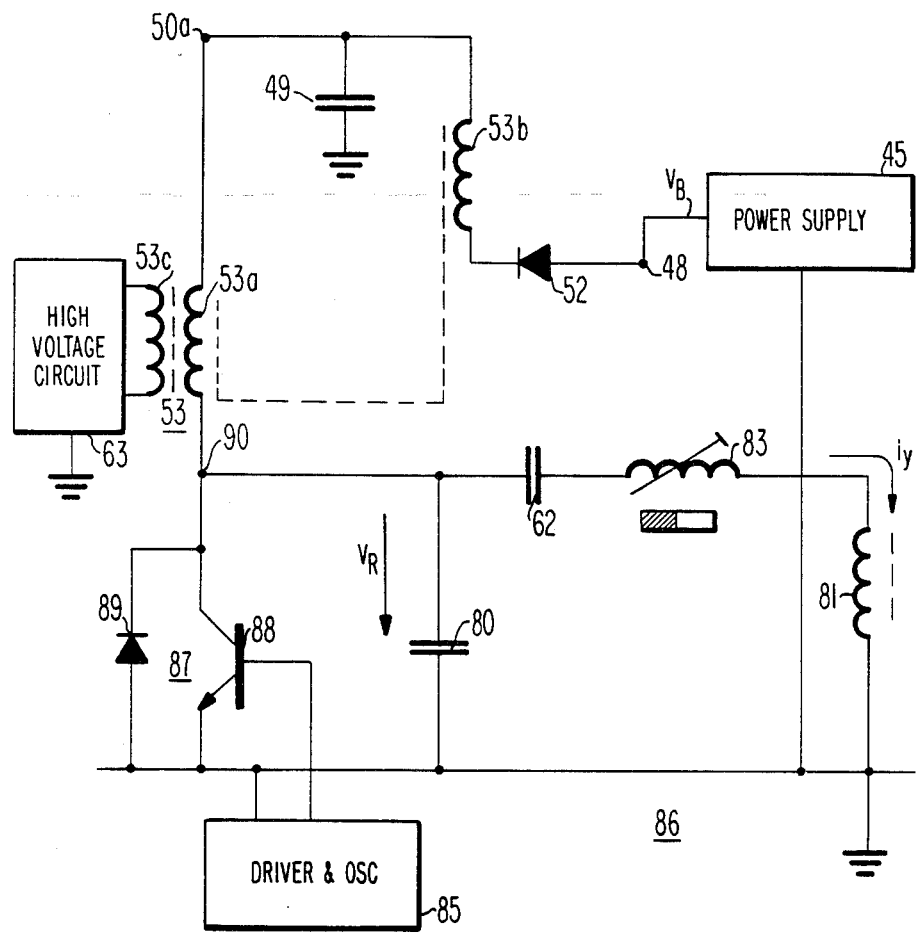
FIG. 4 illustrates a third embodiment of a deflection circuit embodying the invention.

FIGS. 3 and 4 illustrate alternative embodiments, respectively, of deflection circuit 200 of FIG. 1. Identical numbers in FIGS. 1, 3 and 4 indicate similar items or functions. The principle of operation of deflection circuit 200' or 200" of FIGS. 3 and 4, respectively, in which raster width circuit 70 and flyback transformer 53 of FIG. 1 are modified with respect to FIG. 1, is similar to that of deflection circuit 200 of FIG. 1. In deflection circuit 200' of FIG. 3, for example, filter capacitor 49 is coupled between terminal 50a and ground. Capacitor 49 of FIG. 3 is of a higher voltage rating than capacitor 49 of FIG. 1. In deflection circuit 200" of FIG. 4, for example, winding 53b, which replaces inductor 51 of FIG. 1 is coupled by mutual inductance to flyback transformer 53. Winding 53b of FIG. 4 is coupled to one plate of capacitor 49. The junction between capacitor 49 and winding 53b of FIG. 4 is coupled to terminal 50a of the primary winding of flyback transformer 53. Primary winding 53a of transformer 53 of FIG. 4 requires the same number of turns as the combination of windings 53a and b of circuit 200 of FIG. 1. Advantageously, in circuit 200" of FIG. 4 inductor 51 of FIG. 1 is saved because the leakage inductance is used instead.

What is claimed is:

1. A deflection system with raster width control, comprising:
   a deflection winding;
   a deflection generator coupled to said deflection winding for generating a trace scanning current and a retrace scanning current in said deflection winding that define corresponding trace and retrace intervals in a deflection period;
   a transformer coupled to said deflection generator and including first and second transformer windings in which an alternating current deflection rate voltage is developed;
   an ultor circuit coupled to said second transformer winding to produce an ultor voltage that draws a load current from said second transformer winding;
   a source of energizing voltage coupled to said transformer;
   an inductance coupled to said transformer for conducting in said inductance a current representative of said load current;
   switching means responsive to said voltage in said transformer for decoupling said inductance from said transformer during an interval in said deflection period in which said voltage in said transformer is at a first polarity, and for coupling said inductance to said transformer during the entire interval in said deflection period in which said voltage in said transformer is at the opposite polarity to cause the flow of said current in said inductance, wherein during the time in which said voltage in said transformer is at said opposite polarity, said current in said inductance develops a self-induced voltage in said inductance that is representative of said load current;
   means responsive to said self-induced voltage that is representative of said load current for developing at a terminal of said first transformer winding a first voltage that controls the amplitude of said trace scanning current, wherein a change in the value of said load current causes a sufficient change in the value of said current in said inductance such that said change in the value of said current in said inductance by itself produces in said inductance a different value of said self-induced voltage to obtain a corresponding different value of said first voltage and of said trace scanning current for controlling the raster width.

2. The deflection system as recited in claim 1, wherein said switching means includes a rectifier coupled to said transformer that rectifies said deflection rate voltage by an amount that is controlled by said self-induced voltage in said inductance to produce a corresponding different value of a trace voltage.

3. The deflection system as recited in claim 2, wherein said rectifier comprises a two-terminal diode.

4. The deflection system as recited in claim 2, wherein the opposite polarity of said deflection rate voltage in said deflection transformer forward biases said rectifier to develop said current in said inductance that replenishes energy losses in said deflection winding and said first polarity of said deflection rate voltage in said deflection transformer decreases said current in said inductance sufficiently to commutate off said rectifier.

5. The deflection system as recited in claim 4 wherein said rectifier is forward biased during a portion of the retrace interval that varies in duration in accordance with said load current.

6. The deflection system as recited in claim 1 wherein said first voltage developing means comprises a first capacitor that is coupled to said terminal of said first transformer winding for developing a direct current voltage thereat.

7. The deflection system as recited in claim 6, wherein said first capacitor is series coupled with said source of energizing voltage to produce said first voltage that is the sum of the voltage across said capacitor and the voltage of said source of energizing voltage.

8. The deflection system as recited in claim 1, wherein said deflection generator comprises a trace capacitor that supplies said trace scanning current, and wherein said first voltage is coupled to a plate of said trace capacitor for controlling the voltage across said trace capacitor.

9. The deflection system as recited in claim 8, wherein said first voltage is coupled to said plate of said trace capacitor for substantially charging said trace capacitor to the voltage of said first voltage.

10. The deflection system as recited in claim 1, wherein said deflection generator, inductance and deflection winding form a retrace resonance circuit during the retrace interval and are coupled in a manner to reduce variations in the retrace time as said load current varies.

11. The deflection system as recited in claim 10, wherein said switching means includes a rectifier coupled to said inductance, said rectifier being forward biased during a portion of the retrace interval that varies in duration in accordance with said load current, and wherein said rectifier couples said inductance within said retrace resonance circuit in a manner to stabilize the resonance frequency thereof as said load current varies.

12. The deflection system as recited in claim 11, wherein said inductance tends to increase the resonance frequency of said retrace resonance circuit when said rectifier is forward biased and decrease the retrace resonance frequency when said rectifier is commutated off.

13. The deflection system as recited in claim 1, wherein said first voltage is developed at one end terminal of said first transformer winding.

14. The deflection system as recited in claim 13, wherein said first transformer winding includes an intermediate tap terminal for coupling said current in said inductance to said deflection generator.

15. The deflection system as recited in claim 1, wherein said inductance is magnetically coupled to said deflection transformer.

16. The deflection system as recited in claim 1, wherein said inductance is included in said first transformer winding.

17. The deflection system as recited in claim 16, wherein said inductance is coupled between one end terminal of said first transformer winding and an intermediate tap terminal thereof.

18. The deflection system as recited in claim 17, wherein said first voltage developing means comprises a capacitor coupled between said intermediate tap and a common conductor of said deflection system for developing said first voltage between said intermediate tap terminal and said common conductor of said deflection system.

19. The deflection system as recited in claim 1, wherein the amplitude of said first polarity of said deflection rate voltage determines the range of variations of said trace scanning current that can be produced by said first voltage developing means.

20. A deflection system with retrace interval stabilization, comprising:
   a deflection winding;
   a deflection generator coupled to said deflection winding for generating a trace scanning and a retrace scanning current in said deflection winding that define corresponding trace and retrace intervals in each deflection period, including a retrace capacitor that form a retrace resonance circuit with said deflection winding;
   a transformer coupled to said deflection generator and including first and second transformer windings in which an alternating current deflection rate voltage is developed;
   a source of energizing voltage coupled to said transformer;
   a load circuit coupled to said second transformer winding that draws a load current from said second transformer winding;
   an inductance;
   a diode for coupling said inductance to said retrace resonance circuit within said retrace interval, said diode developing an input current in said inductance that is related to said load current and that produces a self-induced voltage in said inductance, wherein said diode becomes forward biased into conducting said input current when said deflection rate voltage changes polarity to a first polarity and wherein a second polarity of said deflection rate voltage in said transformer decreases said input current sufficiently to commutate off said diode such that said diode couples said inductance to said retrace resonance circuit during a portion of the retrace interval having a duration that varies in accordance with said load current so as to vary in accordance with said load current the resonance frequency of said retrace resonance circuit for stabilizing the retrace interval; and
   means responsive to said self-induced voltage that is representative of said load current for developing at a terminal of said first transformer winding a first voltage that controls the amplitude of said trace scanning current, wherein a change in the value of said load current causes a sufficient change in the value of said current in said inductance such that said change in the value of said current in said inductance by itself produces in said inductance a different value of said self-induced voltage to obtain a corresponding different value of said first voltage and of said trace scanning current for controlling the raster width.

* * * * *